United States Patent [19]

Hubbard et al.

[11] 4,406,281
[45] Sep. 27, 1983

[54] FLUID IMPERMEABLE COVER FOR OPERATING ROOM TOURNIQUET

[75] Inventors: Vance M. Hubbard, Euless; Welton K. Brunson, Bedford, both of Tex.

[73] Assignee: Tecnol, Inc., Ft. Worth, Tex.

[21] Appl. No.: 254,193

[22] Filed: Apr. 14, 1981

[51] Int. Cl.³ .............................................. A61B 19/00
[52] U.S. Cl. ................................. 128/132 R; 128/327
[58] Field of Search ............... 128/327, 686, 299, 157, 128/132 R

[56] References Cited

U.S. PATENT DOCUMENTS

| | | | |
|---|---|---|---|
| 2,533,924 | 12/1950 | Foley | 128/327 X |
| 3,654,931 | 4/1972 | Hazlewood | 128/327 |
| 4,139,003 | 2/1979 | Little et al. | 128/157 |

*Primary Examiner*—Michael H. Thaler

*Attorney, Agent, or Firm*—Jerry W. Mills

[57] ABSTRACT

The specification discloses a cover for protecting a hospital operating room tourniquet. A thin sheet (12) is formed from flexible, liquid impervious material and has a length sufficient to be wrapped around the limb of a patient. A pad (14) is formed along one side of the sheet in order to be wrapped around the patient's limb to perform cushioning thereto. A fastener (26-28) is attached to one edge of the sheet and is attached to another portion of the sheet in order to maintain the sheet in the desired position about the patient's limb such that a tourniquet can be placed thereover. The sheet has a width wider than the tourniquet such that a portion of the flexible sheet may be folded over the tourniquet to cover and shield the tourniquet from moisture and contamination.

12 Claims, 6 Drawing Figures

FLUID IMPERMEABLE COVER FOR OPERATING ROOM TOURNIQUET

SUMMARY OF THE INVENTION

This invention relates to a disposable article for use in a hospital, and more particularly relates to a fluid impermeable cover for a hospital operating room tourniquet.

SUMMARY OF THE PRIOR ART

In many hospital environments, it is necessary to place a tourniquet around a limb or other portion of a patient's body in order to reduce or control the flow of blood to the limb. Various tourniquets have been designed for this purpose, one of the most successful comprising a flexible member which may be wrapped around the patient's limb and then inflated by air in order to exert pressure around the limb.

Such tourniquets are often used in conjunction with an operation or other medical procedure which requires sterilization of the patient's limb. When this occurs, various sterilized or preping solutions are applied to the limb, and often such preping solution comes into contact with the tourniquet. It is also common to use absorbent gauze sponges or bandage rolls between the tourniquet and the patient's limb in order to prevent pinching of the patient's skin upon inflation of the tourniquet. The absorbent materials tend to soak in the preping solution and can cause irritation of the patient's skin.

In the past, hospital staffs have attempted to improvise various covers for operating room tourniquets to protect the tourniquets from the preping solution. Commonly, absorbent surgical towels have been placed over the tourniquet. Not only is it time consuming and inconvenient to improvise padding and covers for operating room tourniquets, the items commonly used are relatively expensive and must be cleaned thereafter. Because prior padding and covers heretofore used are absorbent, the tourniquet is not protected against preping solution, since the preping solution soaks through the absorbent materials to the surface of the tourniquet.

Moreover, the sponges or bandage rolls used under the touniquet sometimes become uneven cushions against the patient's skin, thereby creating patient discomfort. Further, the absorbent sponges or bandage rolls allow the preping solution to be absorbed between the skin and the tourniquet, rather than repelled, thereby creating discomfort over the length of the operation or procedure. Because operating room tourniquets are often sequentially used on multiple patients, the tourniquets may become contaminated and therefore cause staph infections to be transmitted between patients.

A need has thus arisen for a tourniquet cover which can provide a smooth padding between the skin of the patient and the tourniquet and which can also completely cover the tourniquet to prevent contamination by preping solution, bacteria or the like.

SUMMARY OF THE INVENTION

The present invention relates to a tourniquet cover which substantially minimizes, reduces or eliminates the problems heretofore associated with the use of operating room tourniquets.

In accordance with the present invention, a tourniquet cover for use in a hospital includes a thin sheet of liquid impervious material having a length sufficient to be wrapped around a limb of a patient. A padded portion is formed along one side of the sheet for being wrapped around the patient's limb to provide cushioning thereto. A fastener is fastened to one edge of the sheet and may be fastened to another portion of the sheet in order to maintain the sheet about the patient's limb such that a tourniquet can be placed thereover. The sheet includes a width wider than the tourniquet such that a portion of the flexible sheet may be folded over the tourniquet to cover and shield the tourniquet from moisture and contamination.

In accordance with a more specific aspect of the present invention, a cover for an operating room tourniquet includes a thin flexible sheet of liquid impervious elastomeric material having a length sufficient to be wrapped around a limb of a patient and having a width greater than the width of an operating room tourniquet. A pad is attached along one side of the flexible sheet for being wrapped around the limb of the patient to provide cushioning thereto. The pad has a length equal to the length of the flexible sheet and a width generally equivalent to the width of an operating room tourniquet. The flexible sheet and the pad may be stretched when wrapped around the limb of the patient in order to provide a tight fit thereto. A fastener enables one end of the flexible sheet to be fastened to another portion of the flexible sheet to maintain the position of the flexible sheet about the limb of the patient. The flexible sheet includes a portion not covered by the pad or the tourniquet for being folded over the operating room tourniquet affixed over the sheet and the pad in order to cover and shield the operating room tourniquet from moisture and contamination.

In accordance with yet another aspect of the invention, a method of shielding a hospital tourniquet includes positioning a thin liquid impervious sheet around the limb of a patient. A tourniquet is disposed over the sheet around the limb of the patient, the sheet having a larger width then the width of the tourniquet. An edge portion of the sheet is folded over the tourniquet and covers the outer portion of the tourniquet to protect the tourniquet from the moisture and contamination.

DESCRIPTION OF THE DRAWINGS

For a more complete understanding of the present invention and for further objects and advantages thereof, reference is now made to the following drawings.

DESCRIPTION OF THE PREFERRED EMBODIMENT

Figure 1:
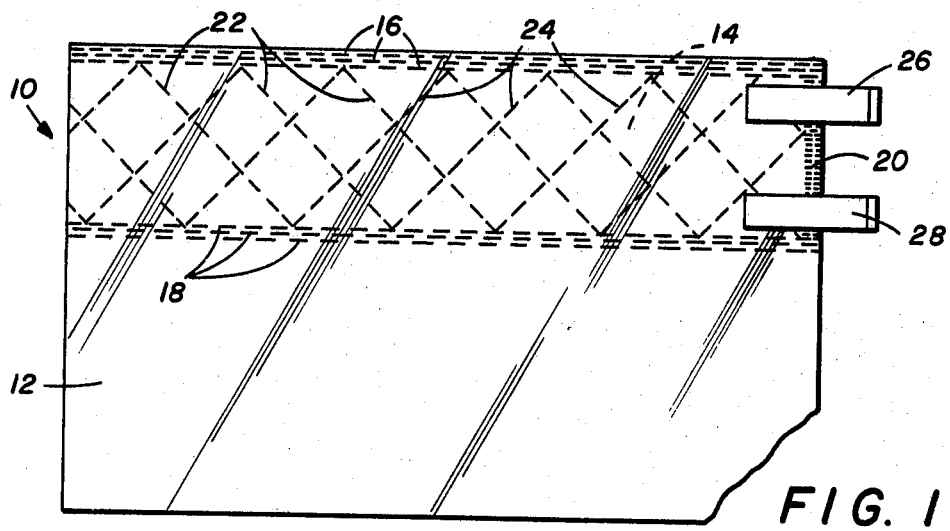
FIG. 1 is a top view of the present tourniquet cover.

Referring now to the drawings wherein like reference characters designate like and corresponding parts throughout the several views, there is shown in FIG. 1 the present tourniquet cover of the invention designated by reference numeral 10. Cover 10 comprises a rectangular, thin plastic sheet 12 which may be constructed from any suitable thin, flexible elastomeric material which is impervious to water. In the preferred embodiment, sheet 12 is formed from thin plastic material made by Shell Oil Corporation under the designation Kraton 2109 thermoplastic rubber and formed into a thin, flexible elastomeric sheet by the Clopay Corporation. Sheet 12 is preferably of 4.5 to 5 mil in thickness and is substantially impervious to water and moisture in order to provide protection to the tourniquet from preping solutions and the like.

An important aspect of the invention is that the sheet 12 is stretchable, as will be subsequently described in greater detail. While it will be understood that sheet 12 may vary in dimensions for various uses, dimensions which have been found to work well in practice comprise a rectangular sheet from 13 to 14 inches wide and from 20 to 22 inches long. A larger version having dimensions of approximately 13 inches in width and 33 inches in length has been found useful for larger applications.

A pad or padded section 14 is affixed along one side of the sheet 12. In FIG. 1, the padded section 14 is attached to the rear side of sheet 12, while in FIG. 2 the padded section 14 is directly shown. Referring to FIG. 1, it may be seen that the padded section has a width less than the width of sheet 12. While the relative dimensions of the sheet and the padded section 14 may vary in accordance with particular desired usages, in the preferred embodiment the padded section 14 has a width of less than half the width of the sheet 12. A preferred width of the padded section 14 comprises, for example, from 4½ to 5 inches in width, although this width could be varied as noted above. The padded section 14 is formed from any suitable relatively thin and flexible pad, such as the four ounce needle punch polyester padding manufactured and sold by National Felt Company.

The padded section 14 is bonded in the preferred embodiment to sheet 12 by ultrasonic bonding. Stitch lines formed by the bonding process 16 may be seen in FIG. 1 and serve to affix one edge of the padded section 14 along the outer edge of sheet 12. Elongated stitches 18 bond the opposite side of the padded section 14 to the general mid-region of sheet 12. The end regions of the padded section 14 may be bonded to sheet 12 by stitches 20, although in some instances one or more ends of the padded section 14 will remain unstitched as shown in FIGS. 1 and 2.

The body of the padded section 14 is additionally attached to sheet 12 by means of diagonal stitches 22 and 24. Stitches 22 run diagonally across the body of the padded section 14 at an angle to the length of the padded section 14. Stitches 24 run in opposite directions to stitches 22. The diagonal stitching formed by stitches 22 and 24 operates to allow some stretching of the padded section 14 when the sheet 12 is stretched. This enables the cover to be stretched about the limb of a patient to provide a very tight fit in order to tend to prevent moisture from being absorbed between the padded section 14 and the skin of the patient. In the preferred embodiment, the stitches 16, 18, 20, 22 and 24 are formed by ultrasonic bonding. An ultrasonic bonding unit is moved relative to the assembled sheet 12 and padded section 14 and the stitches 16, 18, 20, 22 and 24 are formed as illustrated in order to bond the sheet 12 and the padded section 14 together.

Figure 2:
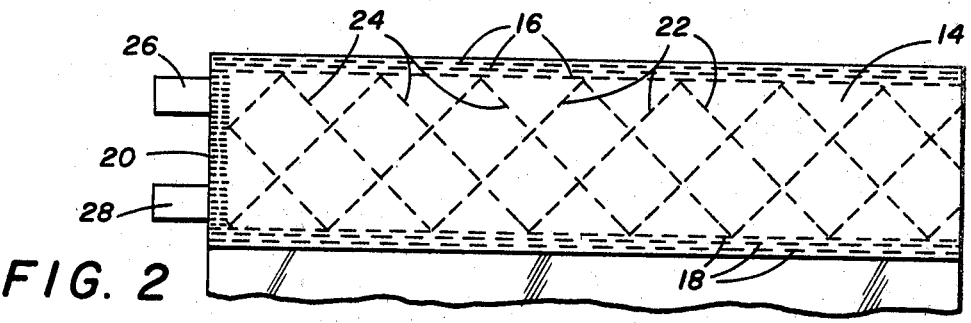
FIG. 2 is a view of the back of the cover shown in FIG. 1, partially broken away.

FIG. 2 illustrates a top view of the padded section 14 and further illustrates the ultrasonic bonding stitches 16-24 from the reverse side as previously shown in FIG. 1. An advantage of the ultrasonic welding technique utilized with the present invention is that a secure bond is provided, without the requirements of thread or other material which would tend to reduce the padding effect provided by the padded section 14. The ultrasonic bonding technique is also a very quick and inexpensive technique of manufacture of the present goods.

Fasteners 26 and 28 comprise in the preferred embodiment strips of tape having one-half the length thereof attached to an end of sheet 12 as illustrated. Fasteners 26 and 28 are applied above the padded section 14 as illustrated. Instead of two fasteners, it of course will be possible to use a greater or lesser number of fasteners and it will also be understood that other types of fasteners could also be utilized. Normally, the exposed ends of fasteners 26 and 28 are covered by removable material such that the sticky portions of the tapes are not exposed until they are decided to be used. The sticky surfaces of the fasteners 26 and 28 are illustrated in FIG. 2.

Figure 3:
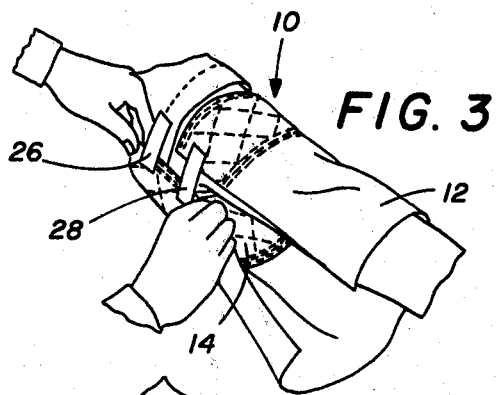
FIG. 3 is a somewhat diagrammatic perspective view of the initial attachment of the present cover around the limb of a patient.

FIGS. 3-6 illustrate the sequential procedure for application and use of the present tourniquet cover. Referring to FIG. 3, the cover 10 is first wrapped around the limb of a patient. In the illustrated embodiment, it is desired to apply a tourniquet to the upper arm of a patient. The padded section 14 is placed around the skin of the patient, with the sheet 12 being disposed outwardly. One end of the padded section 14 is pressed against the patient's arm and the padded section 14 and the sheet 12 are stretched and wrapped about the patient's arm. The stretching of the sheet 12 and paddes section 14 applies a very tight fit to the arm.

The stitches bonding the sheet 12 and the padded section 14 together provide give so that the padded section 14 may be tightly pressed against the patient's skin without wrinkling or causing pain. Once the padded section 14 and sheet 12 have been wrapped around the arm of a patient, the material covering the adhesive portions of the fasteners 26 and 28 is removed and the fasteners 26 and 28 are pressed down on a portion of the sheet 12. In this position, the padded section 14 and the sheet 12 are held around the patient's arm.

Figure 4:
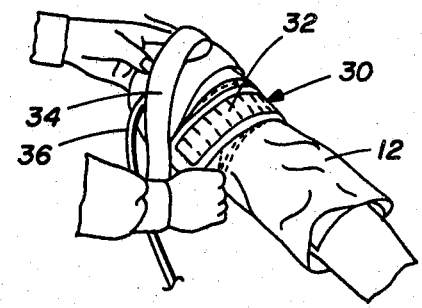
FIG. 4 is a somewhat diagrammatic view illustrating the placement of an operating room tourniquet over the present cover.

As shown in FIG. 4, the next step is to wrap a conventional "OR" tourniquet 30 around the patient's arm directly over the sheet 12 and padded section 14. Any suitable type of "OR" tourniquet may be used in conjunction with the present cover, such as the "OR" tourniquets manufactured and sold by Kidde Corporation and others. The conventional "OR" tourniquet will comprise an inflatable portion 32 and a cover strap 34 which is wrapped tightly around the arm of the patient. An inflating tube 36 extends from the inflatable portion 32. As shown in FIG. 4, over one-half of the area of the sheet 12 is uncovered after placing of the "OR" tourniquet 30.

Figure 5:
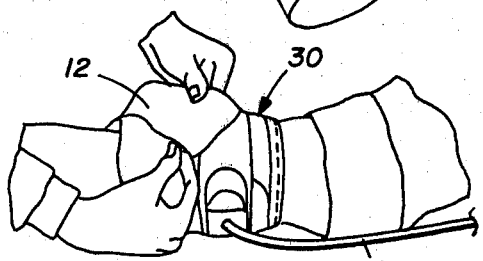
FIG. 5 is a somewhat diagrammatic view illustrating the folding back of the present cover over the tourniquet.
Figure 6:
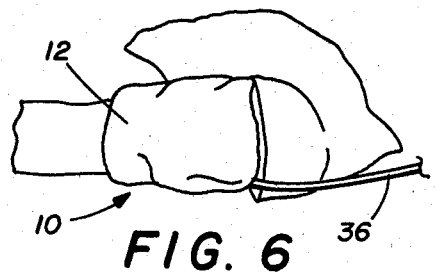
FIG. 6 is a somewhat diagrammatic view illustrating the present cover placed over and protecting an operating room tourniquet when in use.

After the "OR" tourniquet is properly positioned on the patient's arm as shown in FIG. 5, the lower portion of the sheet 12 is folded back over the tourniquet. The sheet 12 is dimensioned to fully cover the tourniquet 30, and the final position of the cover 10 over the tourniquet is illustrated in FIG. 6. As shown in FIGS. 5 and 6, the inflation tube 36 extends out from under the cover 12 so that air may be forced through the tube into the expandable portion 32 of the tourniquet in order to apply the tourniquet to the patient's limb.

FIG. 6 illustrates the advantages of the present invention in that the entire "OR" tourniquet is covered by a fluid impermeable sheet during the operation or procedure being performed on the patient's limb. If desired, tape may be applied about one or more edges of the cover 10 in order to prevent any fluid or moisture from entering between the padded section 14 and the patient's limb. Preping solution may be applied to the patient's limb and applied directly over the cover 10, without the tourniquet 30 being exposed to the preping solution. Consequently, after use of the "OR" tourniquet, the tourniquet may be used on other patients without fear of cross-contamination from one patient to another. Moreover, the "OR" tourniquets, when used with the present invention, are not subject to the deleterious affects of preping solution and other chemicals often used during medical procedures or operations.

When it is desired to remove the "OR" tourniquet used with the present cover, the procedure shown in FIGS. 3-6 is reversed. The end of the sheet 12 is peeled back from the tourniquet and the tourniquet removed. The fasteners 26 and 28 are then removed and the present cover removed. The present cover is constructed in a very inexpensive manner so that it may be disposed of to prevent contamination from one patient to another.

It will thus be seen that the present cover provides many advantages in use in a hospital environment. The padded section 14 provides a substantial amount of comfort to the patient when used in conjunction with a tourniquet. The construction of the cover involving the stretchable sheet 12 in combination with the particular stitching bonding the sheet 12 with the padded section 14 enables stretching of the pad evenly about the limb of a patient, thereby preventing wrinkling and discomfort to the patient. The complete covering of the tourniquet by a fluid impervious sheet of material prevents contamination and damage to the tourniquet. The device is inexpensively constructed and therefore may be disposed of after use. With the use of the present cover, additional use of bandages, towels or the like is eliminated. The present invention is very easy to apply and therefore saves valuable manpower.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. A tourniquet cover for use in a hospital comprising:
   a thin flexible sheet of liquid impervious material having a length dimension and a width dimension, the length dimension sufficient to be wrapped around a limb of a patient more than a full revolution to provide overlap of the ends thereof;
   a padded layer disposed adjacent one edge of said sheet along the length dimension thereof and attached thereto for being wrapped around the patient's limb to provide cushioning thereto, said padded layer dimensioned along the width thereof less than one half the width of said sheet;
   means for fastening one edge of said sheet along the width dimension thereof to a portion of said sheet in order to maintain said sheet about the patient's limb with said padded layer adjacent the patient's limb such that a tourniquet can be placed over the portion of said sheet adjacent said padded layer, the tourniquet being protected from the skin of the patient by said sheet and said padded layer preventing the skin of the wearer from being pinched by the tourniquet; and
   said padded layer having a width dimension wider than the tourniquet such that the portion of said flexible sheet not adjacent to said padded layer may be folded over the outer surface of the tourniquet to fully cover and shield the tourniquet from moisture and contamination.

2. The tourniquet cover of claim 1 wherein said padded portion is ultrasonically bonded to said sheet.

3. The tourniquet cover of claim 1 wherein said sheet is rectangular and is formed from thin flexible elastomeric material.

4. The tourniquet cover of claim 3 wherein said padded portion is bonded to said sheet to allow stretching of said sheet without damage to said bond between said padded portion and said sheet.

5. The tourniquet cover of claim 3 wherein said padded portion covers less than one-half the surface area of said sheet.

6. The tourniquet cover of claim 1 wherein said fastening means comprises tape attached at one end to one edge of said sheet and having an adhesive end for attaching to a portion of said sheet.

7. A cover for an operating room tourniquet comprising:
   a thin flexible sheet of liquid impervious elastomeric material having a length dimension and a width dimension, the length dimension sufficient to be wrapped around a limb of a patient more than a full revolution to provide overlap of the ends thereof and having a width greater than the width of an operating room tourniquet;
   a pad attached along the length dimension on one side of said flexible sheet for being wrapped around the limb of the patient between the limb and said sheet to provide cushioning for the limb, said pad having a length substantially equal to the length of said flexible sheet and a width at least as wide as an operating room tourniquet but less than one half the width of said sheet;
   said flexible sheet and said pad stretching when wrapped around the limb of the patient;
   means for fastening one end of said flexible sheet to another portion of said flexible sheet to maintain the position of said flexible sheet around the limb of the patient; and
   the portion of said flexible sheet not covered by said pad operable to be folded over the operating room tourniquet affixed over the portion of said sheet adjacent said pad in order to cover and shield the inner and outer surfaces of the operating room tourniquet from moisture and contamination, while preventing the skin of the patient from being pinched by the tourniquet.

8. The cover for an operating room tourniquet of claim 7 wherein said pad is attached to said sheet by stitches which are angled with respect to the side edges of said pad and said sheet in order to allow stretching of said pad and said sheet.

9. The cover for an operating room tourniquet of claim 8 wherein said stitches are formed by ultrasonic bonding.

10. A method of shielding a hospital tourniquet comprising:

positioning a thin liquid impervious sheet around the limb of a patient more than one complete revolution;

disposing a tourniquet over the sheet adjacent one edge thereof around the limb of the patient to leave one edge of the sheet uncovered, the tourniquet having a width less than one half the width of the sheet; and folding the free edge portion of the sheet over the tourniquet and covering the outer portion of the tourniquet to protect the inner and outer surfaces of the tourniquet from moisture and contamination, while preventing the skin of the patient from being pinched by the tourniquet.

11. The method of claim 10 wherein the sheet is flexible and further comprising:

stretching the sheet around the limb of the patient to ensure a tight fit of the shield and the tourniquet.

12. The method of claim 10 and further comprising:

placing a flexible pad attached to the sheet between the limb of the patient and the sheet.

* * * * *

UNITED STATES PATENT AND TRADEMARK OFFICE
CERTIFICATE OF CORRECTION

PATENT NO. : 4,406,281

DATED : September 27, 1983

INVENTOR(S) : Vance M. Hubbard and Welton K. Brunson

It is certified that error appears in the above-identified patent and that said Letters Patent is hereby corrected as shown below:

Col. 4, line 31, "placed around" should be --placed against--.

Col. 4, line 36, "paddes" should be --padded--.

Signed and Sealed this

Fifteenth Day of May 1984

[SEAL]

Attest:

GERALD J. MOSSINGHOFF

Attesting Officer

Commissioner of Patents and Trademarks